United States Patent
Matsumoto et al.

(10) Patent No.: US 12,171,618 B2
(45) Date of Patent: Dec. 24, 2024

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventors: Tsuyoshi Matsumoto, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 137 days.

(21) Appl. No.: 18/061,882

(22) Filed: Dec. 5, 2022

(65) Prior Publication Data

US 2023/0172587 A1 Jun. 8, 2023

(30) Foreign Application Priority Data

Dec. 8, 2021 (JP) .................................. 2021-199222

(51) Int. Cl.
- A61B 8/00 (2006.01)
- A61B 8/08 (2006.01)
- G06T 7/20 (2017.01)

(52) U.S. Cl.
CPC .............. *A61B 8/54* (2013.01); *A61B 8/085* (2013.01); *A61B 8/4263* (2013.01); *A61B 8/463* (2013.01); *G06T 7/20* (2013.01); *G06T 2207/20081* (2013.01)

(58) Field of Classification Search
CPC .......... A61B 8/54; A61B 8/085; A61B 8/4263
See application file for complete search history.

(56) References Cited

U.S. PATENT DOCUMENTS

| | | | |
|---|---|---|---|
| 2019/0142390 A1 | 5/2019 | Luo et al. | |
| 2019/0183462 A1* | 6/2019 | Yang | ........... G06F 18/2431 |
| 2021/0312652 A1 | 10/2021 | Padwal et al. | |

FOREIGN PATENT DOCUMENTS

JP 2021-506470 A 2/2021

OTHER PUBLICATIONS

The extended European search report issued by the European Patent Office on Apr. 6, 2023, which corresponds to European Patent Application No. 22212039.6-1126 and is related to U.S. Appl. No. 18/061,882.

* cited by examiner

*Primary Examiner* — Gerald Johnson
(74) *Attorney, Agent, or Firm* — Studebaker & Brackett PC

(57) ABSTRACT

There are provided an ultrasound diagnostic apparatus and a control method of the ultrasound diagnostic apparatus which can accurately observe a target site regardless of a user' skill level even in a case where gas is accumulated in an intestine of a subject.

An ultrasound diagnostic apparatus includes an ultrasound probe; an image acquisition unit that performs transmission and reception of ultrasound beams using the ultrasound probe, and acquires a plurality of frames of ultrasound images which are continuous in time and in which a lower abdomen of a subject is imaged; a gas specifying unit that specifies a gas region or a gas condition on the basis of the ultrasound image; a gas change measurement unit that measures a change of the gas region or the gas condition specified by the gas specifying unit in a case where the ultrasound probe is pressed against the subject; and an imaging guide unit that provides guidance on ultrasound image capturing on the basis of the change of the gas region or the gas condition measured by the gas change measurement unit.

20 Claims, 8 Drawing Sheets

ULTRASOUND DIAGNOSTIC APPARATUS AND CONTROL METHOD OF ULTRASOUND DIAGNOSTIC APPARATUS

CROSS-REFERENCE TO RELATED APPLICATIONS

The present application claims priority under 35 U.S.C. § 119 to Japanese Patent Application No. 2021-199222, filed on Dec. 8, 2021. The above application is hereby expressly incorporated by reference, in its entirety, into the present application.

BACKGROUND OF THE INVENTION

1. Field of the Invention

The present invention relates to an ultrasound diagnostic apparatus and a control method of the ultrasound diagnostic apparatus which are used for performing ultrasonography while pressing an ultrasound probe against a subject.

2. Description of the Related Art

In the related art, an ultrasound image representing a tomogram of an inside of the subject is acquired using a so-called ultrasound diagnostic apparatus, and the examination for the subject is performed by checking the acquired ultrasound image. By the way, in the ultrasound image, for example, gas or the like accumulated in the intestine of the subject appears as a so-called artifact in the ultrasound image, and a site to be observed is blocked by the artifact so that a user may not be able to sufficiently observe a site.

In a case where gas accumulated in the intestine of the subject appears as the artifact in the ultrasound image, it is known that gas can be removed from a region in the subject that the user tries to observe, by pressing the ultrasound probe against the subject, for example. As described above, since the countermeasures differ depending on the types of artifacts, for example, as disclosed in JP2021-506470A, an ultrasound diagnostic apparatus that recognizes the types of artifacts in the ultrasound image, and presents a recognition result to the user has been developed so that the user can take correct countermeasures.

SUMMARY OF THE INVENTION

However, in a case where a target site cannot clearly checked by a normal observation method due to gas accumulated in the intestine of the subject, for example, even in a case where the artifact caused by gas can be recognized by the technique disclosed in JP2021-506470A, in many cases, skilled users can accurately observe the target site by sufficiently removing the gas from the region in the subject to be observed, by pressing the ultrasound probe against the subject or the like, but unskilled users could not sufficiently remove the gas, and could not accurately observe the target site in some cases.

The present invention has been made in order to solve such a problem in the related art, and an object of the invention is to provide an ultrasound diagnostic apparatus and a control method of the ultrasound diagnostic apparatus which can accurately observe the target site regardless of the user' skill level even in a case where gas is accumulated in the intestine of the subject.

In order to achieve the object, an ultrasound diagnostic apparatus according to an aspect of the present invention comprises an ultrasound probe; an image acquisition unit that performs transmission and reception of ultrasound beams using the ultrasound probe, and acquires a plurality of frames of ultrasound images which are continuous in time and in which a lower abdomen of a subject is imaged; a gas specifying unit that specifies a gas region or a gas condition on the basis of the ultrasound image; a gas change measurement unit that measures a change of the gas region or the gas condition specified by the gas specifying unit in a case where the ultrasound probe is pressed against the subject; and an imaging guide unit that provides guidance on ultrasound image capturing on the basis of the change of the gas region or the gas condition measured by the gas change measurement unit.

The ultrasound diagnostic apparatus can further comprise a pressing period setting unit that sets a pressing period in which the ultrasound probe is pressed, in which the gas change measurement unit can measure the change of the gas region or the gas condition in the pressing period set by the pressing period setting unit.

The gas change measurement unit can measure a rate of change of the gas region or the gas condition in the pressing period set by the pressing period setting unit.

The ultrasound diagnostic apparatus can further comprise a pressing motion determination unit that determines a pressing motion of the ultrasound probe against the subject on the basis of a motion of the ultrasound probe, in which the gas change measurement unit can measure the change of the gas region or the gas condition in a case where the pressing motion determination unit determines the pressing of the ultrasound probe.

The ultrasound diagnostic apparatus can further comprise a motion sensor that detects a motion of the ultrasound probe, in which the pressing motion determination unit can determine the pressing motion on the basis of the motion of the ultrasound probe detected by the motion sensor.

Further, the ultrasound diagnostic apparatus can further comprise an optical camera that acquires an optical image including at least the ultrasound probe, in which the pressing motion determination unit can determine the pressing motion by analyzing the optical image acquired by the optical camera.

In this case, the pressing motion determination unit can determine the pressing motion of the ultrasound probe by using a trained determination model obtained by learning the motion of the ultrasound probe in the optical image in which the ultrasound probe is imaged.

The pressing motion determination unit can determine a start of the pressing of the ultrasound probe and an end of the pressing of the ultrasound probe as the pressing motion, and the pressing period setting unit can set a period from when the pressing motion determination unit determines the start of the pressing of the ultrasound probe until the pressing motion determination unit determines the end of the pressing of the ultrasound probe, as the pressing period.

Further, the pressing motion determination unit can determine a start of the pressing of the ultrasound probe and a pause during the pressing of the ultrasound probe as the pressing motion, and the pressing period setting unit can set a period from when the pressing motion determination unit determines the start of the pressing of the ultrasound probe until a predetermined time elapses after the pressing motion determination unit determines the pause of the ultrasound probe, as the pressing period.

The gas specifying unit can specify the gas region or the gas condition by calculating an area of a region having brightness equal to or lower than a predetermined threshold value in the ultrasound image.

The gas specifying unit can specify the gas region or the gas condition on the basis of an image quality of a site shown on a deeper side than an intestinal tract of the subject in the ultrasound image.

The gas specifying unit can specify the gas region or the gas condition by using a trained determination model obtained by learning the gas region or the gas condition in the ultrasound image in which at least the lower abdomen is imaged.

The imaging guide unit can provide guidance to capture the ultrasound image while continuing the pressing of the ultrasound probe in a case where an area of the gas region measured by the gas change measurement unit is reduced or the gas condition measured by the gas change measurement unit is improved.

The imaging guide unit can provide guidance to stop the pressing of the ultrasound probe and to capture the ultrasound image after changing a posture of the subject in a case where an area of the gas region or the gas condition measured by the gas change measurement unit is not changed.

The ultrasound diagnostic apparatus can further comprise a monitor that displays the ultrasound image.

A control method of an ultrasound diagnostic apparatus according to another aspect of the present invention comprises performing transmission and reception of ultrasound beams using an ultrasound probe, and acquiring a plurality of frames of ultrasound images which are continuous in time and in which a lower abdomen of a subject is imaged; specifying a gas region or a gas condition on the basis of the ultrasound image; measuring a change of the specified gas region or gas condition in a case where the ultrasound probe is pressed against the subject; and providing guidance on ultrasound image capturing on the basis of the measured change of the gas region or the gas condition.

According to the present invention, the ultrasound diagnostic apparatus comprises the ultrasound probe; the image acquisition unit that performs transmission and reception of ultrasound beams using the ultrasound probe, and acquires a plurality of frames of ultrasound images which are continuous in time and in which a lower abdomen of a subject is imaged; the gas specifying unit that specifies a gas region or a gas condition on the basis of the ultrasound image; the gas change measurement unit that measures a change of the gas region or the gas condition specified by the gas specifying unit in a case where the ultrasound probe is pressed against the subject; and the imaging guide unit that provides guidance on ultrasound image capturing on the basis of the change of the gas region or the gas condition measured by the gas change measurement unit. Therefore, even in a case where gas is accumulated in an intestine of the subject, a target site can be accurately observed regardless of a user's skill level.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
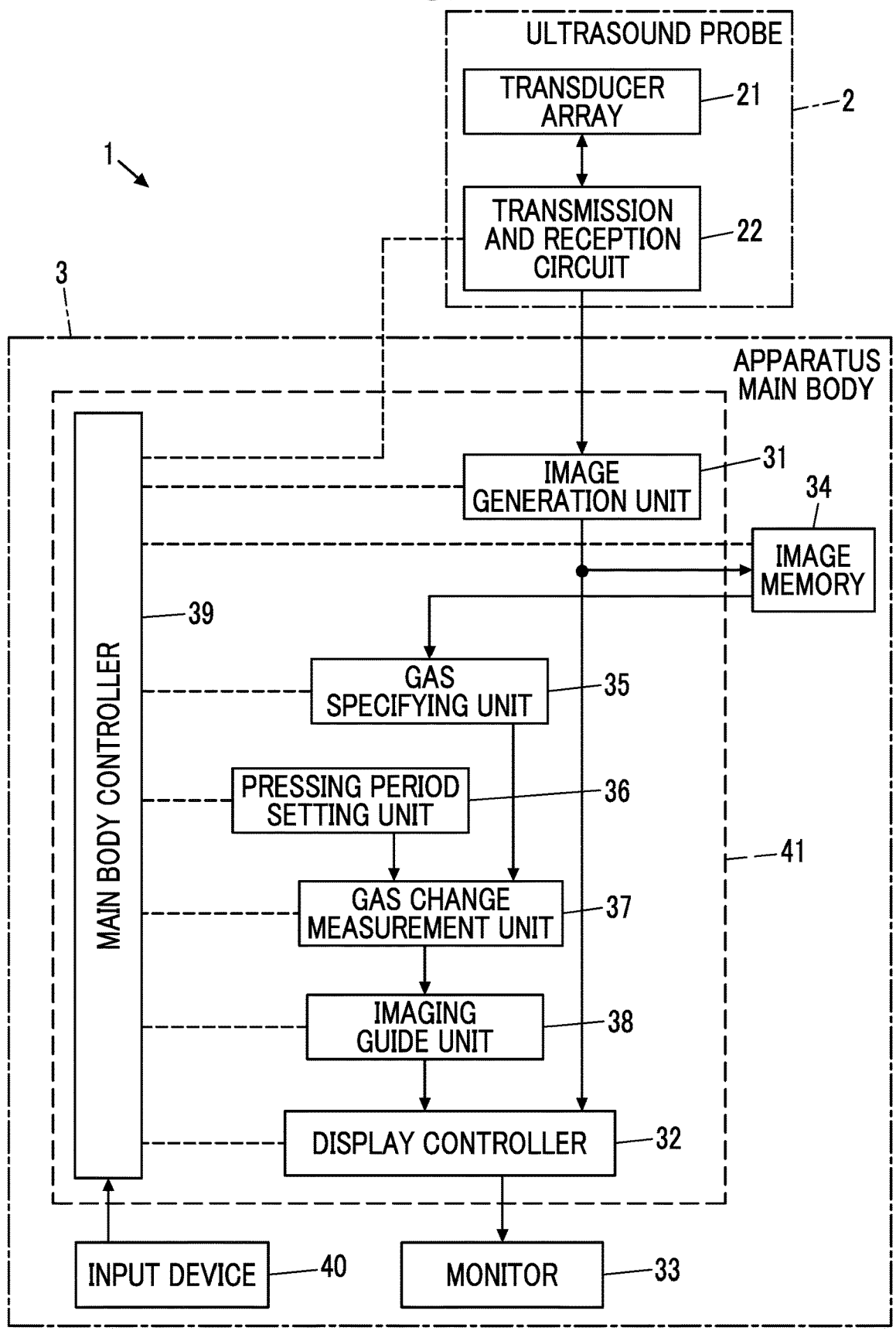
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 comprises an ultrasound probe 2, and an apparatus main body 3 connected to the ultrasound probe 2.

The ultrasound probe 2 comprises a transducer array 21, and a transmission and reception circuit 22 is connected to the transducer array 21.

The apparatus main body 3 comprises an image generation unit 31 connected to the transmission and reception circuit 22 of the ultrasound probe 2. The transmission and reception circuit 22 and the image generation unit 31 constitute an image acquisition unit (not illustrated). Further, a display controller 32 and a monitor 33 are sequentially connected to the image generation unit 31. An image memory 34 is connected to the image generation unit 31. A gas specifying unit 35 is connected to the image memory 34. Further, the apparatus main body 3 comprises a pressing period setting unit 36. A gas change measurement unit 37 is connected to the gas specifying unit 35 and the pressing period setting unit 36. An imaging guide unit 38 is connected to the gas change measurement unit 37. The display controller 32 is connected to the imaging guide unit 38.

In addition, a main body controller 39 is connected to the transmission and reception circuit 22, the image generation unit 31, the display controller 32, the image memory 34, the gas specifying unit 35, the pressing period setting unit 36, the gas change measurement unit 37, and the imaging guide unit 38. An input device 40 is connected to the main body controller 39.

Further, the image generation unit 31, the display controller 32, the gas specifying unit 35, the pressing period setting unit 36, the gas change measurement unit 37, the imaging guide unit 38, and the main body controller 39 constitute a processor 41 for the apparatus main body 3.

The transducer array 21 of the ultrasound probe 2 has a plurality of ultrasonic transducers arranged in a one-dimensional or two-dimensional manner. According to a drive signal supplied from the transmission and reception circuit 22, each of the ultrasonic transducers transmits an ultrasonic wave and receives an ultrasound echo from the subject to output a signal based on the ultrasound echo. For example, each ultrasonic transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
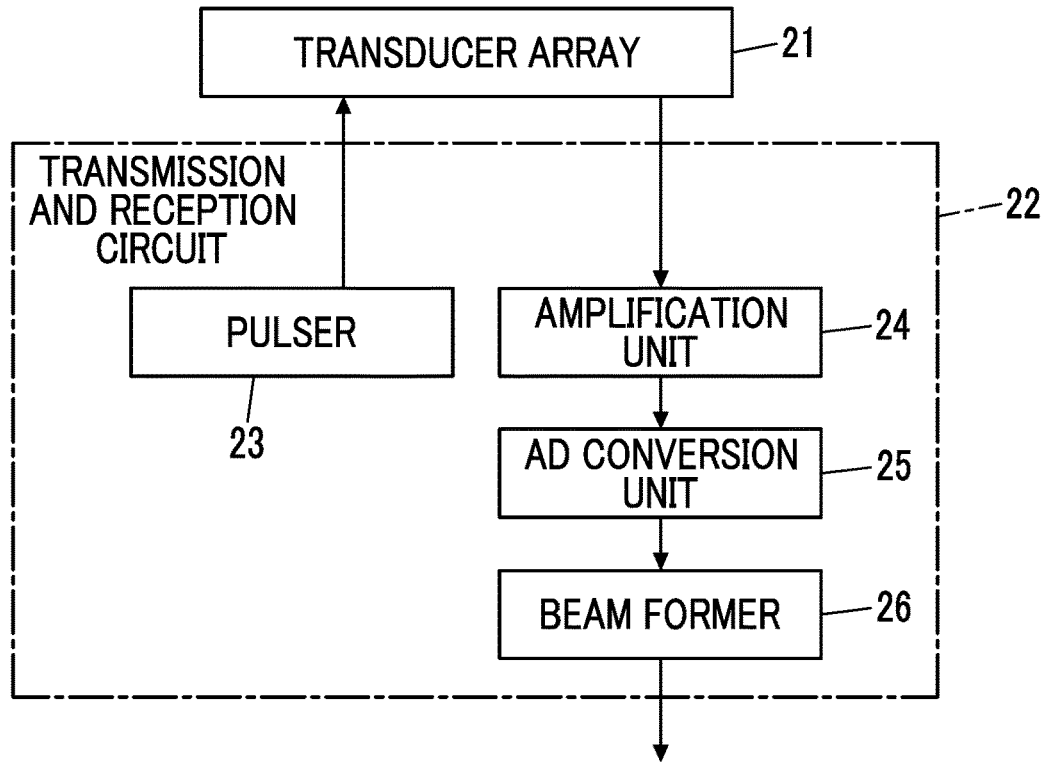
FIG. 2 is a block diagram illustrating a configuration of a transmission and reception circuit in the first embodiment of the present invention.

The transmission and reception circuit 22 causes the transducer array 21 to transmit the ultrasonic wave and generates a sound ray signal on the basis of a reception signal acquired by the transducer array 21, under the control of the main body controller 39. As illustrated in FIG. 2, the transmission and reception circuit 22 has a pulser 23 connected to the transducer array 21, and an amplification unit 24, an analog to digital (AD) conversion unit 25, and a beam former 26 that are sequentially connected in series from the transducer array 21.

The pulser 23 includes, for example, a plurality of pulse generators, and the pulser 23 adjusts the amount of delay of each drive signal so that ultrasonic waves transmitted from the plurality of ultrasonic transducers of the transducer array 21 form an ultrasound beam on the basis of a transmission delay pattern selected according to the control signal from the main body controller 39, and supplies the obtained signals to the plurality of ultrasonic transducers. Thus, in a case where a pulsed or continuous-wave voltage is applied to the electrodes of the ultrasonic transducers of the transducer array 21, the piezoelectric body expands and contracts to generate pulsed or continuous-wave ultrasonic waves from each ultrasonic transducer. From the combined wave of these ultrasonic waves, an ultrasound beam is formed.

The transmitted ultrasound beam is reflected by a target, for example, a site of the subject, and propagates toward the transducer array 21 of the ultrasound probe 2. The ultrasound echo propagating toward the transducer array 21 in this manner is received by each ultrasonic transducer constituting the transducer array 21. In this case, each ultrasonic transducer constituting the transducer array 21 expands and contracts by receiving the propagating ultrasound echo to generate a reception signal that is an electric signal, and outputs the reception signal to the amplification unit 24.

The amplification unit 24 amplifies the signals input from each ultrasonic transducer constituting the transducer array 21, and transmits the amplified signals to the AD conversion unit 25. The AD conversion unit 25 converts the signal transmitted from the amplification unit 24 into digital reception data. The beam former 26 performs so-called reception focusing processing in which addition is performed by giving delays to respective pieces of the reception data received from the AD conversion unit 25. Through the reception focusing processing, a sound ray signal in which each piece of the reception data converted by the AD conversion unit 25 is phased and added and the focus of the ultrasound echo is narrowed is acquired.

Figure 3:
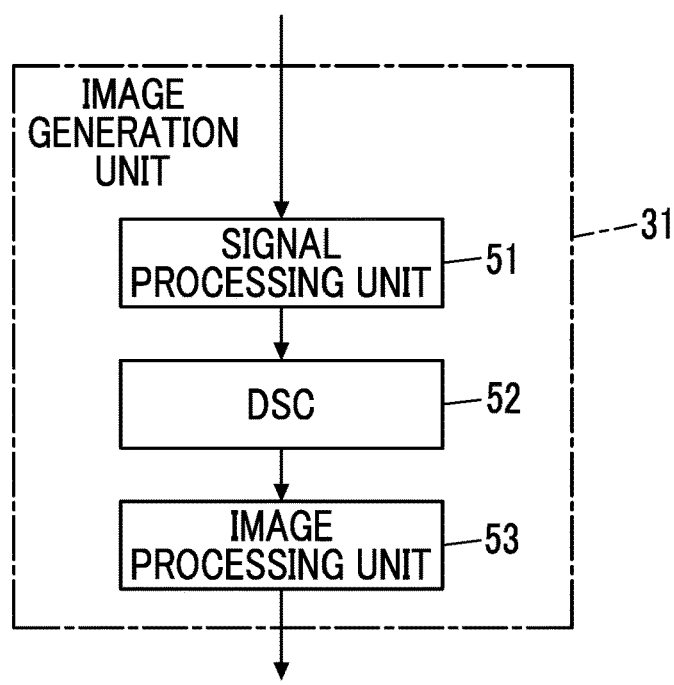
FIG. 3 is a block diagram illustrating a configuration of an image generation unit in the first embodiment of the present invention.

As illustrated in FIG. 3, the image generation unit 31 has a configuration in which a signal processing unit 51, a digital scan converter (DSC) 52, and an image processing unit 53 are sequentially connected in series.

The signal processing unit 51 generates a B-mode image signal, which is tomographic image information regarding tissues inside the subject, by performing, on the sound ray signal received from the transmission and reception circuit 22, correction of the attenuation due to the distance according to the depth of the reflection position of the ultrasonic wave using a sound speed value set by the main body controller 39 and then performing envelope detection processing.

The DSC 52 converts (raster conversion) the B-mode image signal generated by the signal processing unit 51 into an image signal according to a normal television signal scanning method.

The image processing unit 53 performs various kinds of necessary image processing such as gradation processing on the B-mode image signal input from the DSC 52, and then sends the B-mode image signal to the display controller 32 and the image memory 34. In the following, the B-mode image signal subjected to the image processing by the image processing unit 53 is simply referred to as an ultrasound image.

The main body controller 39 controls the transmission and reception circuit 22 of the ultrasound probe 2 and each unit of the apparatus main body 3 according to a program and the like recorded in advance.

The display controller 32 performs predetermined processing on the ultrasound image or the like generated by the image generation unit 31 and displays the ultrasound image or the like on the monitor 33, under the control of the main body controller 39.

The monitor 33 performs various kinds of display under the control of the display controller 32. The monitor 33 includes a display device such as a liquid crystal display (LCD), or an organic electroluminescence (EL) display.

The input device 40 is for a user to perform an input operation. The input device 40 is configured by, for example, a device for a user to perform an input operation, such as a keyboard, a mouse, a trackball, a touchpad, a touch panel, or the like.

Under the control of the main body controller 39, the image memory 34 stores the ultrasound image generated by the image generation unit 31, and sends the stored ultrasound image to the gas specifying unit 35. Here, as the image memory 34, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), and a universal serial bus memory (USB memory) can be used.

Figure 4:
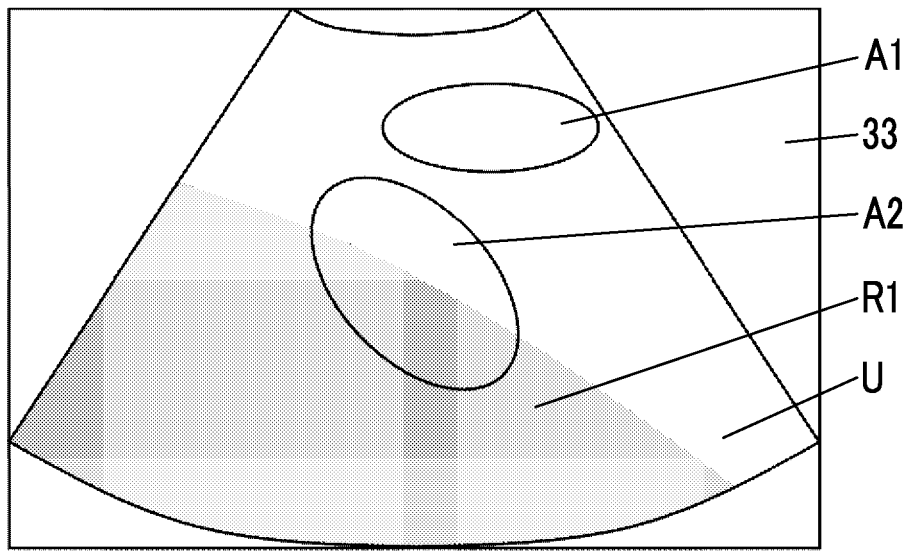
FIG. 4 is an example of an ultrasound image in which gas in a subject is shown as an artifact.

Here, in a case of performing ultrasonography on the lower abdomen of the subject, an examination target site cannot be clearly observed in some cases due to gas accumulated in the intestine of the subject. For example, as illustrated in FIG. 4, gas in the intestine of the subject does not easily transmit ultrasonic waves, and thus may be depicted as a gas region R1, which is a region with low brightness and is called an artifact, in an ultrasound image U. The ultrasound image U illustrated in FIG. 4 includes a kidney A1 and a liver A2 of the subject. However, since the gas region R1 overlaps a part of the liver A2, it is difficult for the user to accurately observe the liver A2.

Figure 5:
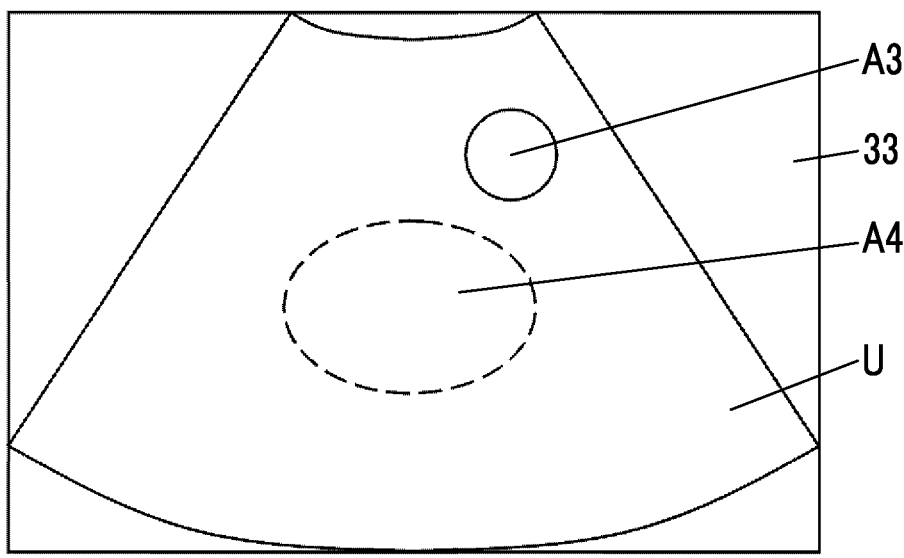
FIG. 5 is an example of an ultrasound image in which a site is unclearly shown due to gas in the subject.

Further, depending on gas conditions including the density, composition, pressure, and the like of gas in the intestine of the subject, the brightness, contrast, and the like of the target site in the ultrasound image may be lowered, that is, the image quality may deteriorate, and thus the site may be unclearly depicted. The deterioration of the image quality is likely to occur in a site that is shown on the deeper side than the intestinal tract. FIG. 5 illustrates an example of the ultrasound image U including a bladder A3, and a uterus A4 shown on the deeper side than the intestinal tract of the subject. In this example, the region of the bladder A3 of the subject is clearly depicted due to a good gas condition, but the region of the uterus A4 is unclearly depicted due to a poor gas condition. Here, the good gas condition means that the gas is in a state of easily transmitting ultrasonic waves because the density of gas is low, the composition of the gas consists of components that easily transmit ultrasonic waves, or the pressure of gas is low, for example. Further, the poor gas condition means that the gas is in a state of not easily transmitting ultrasonic waves because the density of gas is high, the composition of the gas consists of components that do not easily transmit ultrasonic waves, or the pressure of gas is high, for example.

The gas specifying unit 35 specifies the gas region R1 or the gas condition on the basis of the ultrasound image U generated by the image generation unit 31. In this case, the gas specifying unit 35 can specify the gas region R1 or the gas condition by calculating the area of the region having brightness equal to or lower than a predetermined threshold value in the ultrasound image U. As the calculated area is larger, it can be determined that the area of the gas region R1 is large, the gas amount in the intestine of the subject is large, and the gas condition is poor, and as the calculated area is smaller, it can be determined that the area of the gas region R1 is small, the gas amount in the intestine of the subject is small, and the gas condition is good.

The gas specifying unit 35 can specify the gas region R1 or the gas condition on the basis of the image quality of the site shown on the deeper side than the intestinal tract of the subject in the ultrasound image U. Here, the image quality of the site refers to a degree of clearly showing the region representing the site in the ultrasound image U. The fact that the image quality of the site is good means that the site is clearly shown in the ultrasound image U, and that fact that the image quality of the site is poor means that the site is unclear in the ultrasound image U. For example, the gas specifying unit 35 can calculate the image quality of the site on the basis of the brightness, the contrast, the sharpness of the edge, and the like of the site shown on the deeper side than the intestinal tract of the subject. As the image quality of the site shown on the deeper side than the intestinal tract of the subject is poorer, it can be determined that the gas region R1 blocks an observation range and the gas condition is poor, and as the image quality of the site shown on the deeper side than the intestinal tract of the subject is better, it can be determined that the gas region R1 does not block the observation range and the gas condition is good.

The gas specifying unit 35 can specify the gas region R1 or the gas condition by using a trained determination model obtained by learning the gas region R1 or the gas condition in the ultrasound image U in which at least the lower abdomen of the subject is imaged. The trained determination model outputs a specifying result of the gas region R1 or the gas condition in the ultrasound image U in a case where the ultrasound image U is input.

Further, for example, the gas specifying unit 35 can construct the trained determination model by applying a machine learning method described in Csurka et al.: Visual Categorization with Bags of Keypoints, Proc. of ECCV Workshop on Statistical Learning in Computer Vision, pp. 59-74 (2004) or a general image recognition method using deep learning or so-called convolutional neural network (CNN) described in Krizhevsk et al.: ImageNet Classification with Deep Convolutional Neural Networks, Advances in Neural Information Processing Systems 25, pp. 1106-1114 (2012).

For example, the trained determination model can output a coverage degree of the gas or a benign degree of the gas, which represents a degree of the gas region R1 covering the observation range, as the specifying result of the gas region R1 or the gas condition output in a case where the ultrasound image U is input. As the coverage degree of the gas is larger, it can be determined that the gas region R1 blocks the observation range, and as the coverage degree of the gas is smaller, it can be determined that the gas region R1 does not block the observation range. Further, as the benign degree of the gas is greater, it can be determined that the gas condition is good, and as the benign degree of the gas is smaller, it can be determined that the gas condition is poor. Further, the trained determination model can output the area of the region having brightness equal to or lower than the predetermined threshold value in the ultrasound image U or the image quality of the site shown on the deeper side than the intestinal tract of the subject in the ultrasound image U, for example.

The gas specifying unit 35 specifies the gas region R1 and the gas condition for each of the plurality of frames of ultrasound images U continuous in time, which are generated by the image generation unit 31, and sends the specifying result to the gas change measurement unit 37.

In a case of performing the ultrasonography on the lower abdomen of the subject, in a case where the examination target site cannot be clearly observed due to the gas accumulated in the intestine of the subject, for example, a technique is known in which the gas is removed from the region in the subject desired to be observed by the user by pressing the ultrasound probe against the subject, and the target site is observed. Here, in general, the ultrasound probe includes a so-called acoustic lens in order to focus the ultrasonic waves transmitted from the transducer array or the ultrasound echoes that are reflected and propagate from the inside of the subject, and the ultrasound image capturing is performed while the acoustic lens is brought into contact with the body surface of the subject. Pressing the ultrasound probe against the subject is to strongly press the acoustic lens against the subject with a pressure greater than the pressure with which the acoustic lens is brought into contact with the subject in the normal examination.

The pressing period setting unit 36 sets a pressing period in which the ultrasound probe 2 is pressed against the subject. The pressing period setting unit 36 can store, for example, a predetermined time in advance, and set the stored time as the pressing period. Further, the pressing period setting unit 36 can also set a time input by the user via the input device 40, as the pressing period.

The gas change measurement unit 37 measures the change of the gas region R1 or the change of the gas condition specified by the gas specifying unit 35 in a case where the ultrasound probe 2 is pressed against the subject. In this case, the gas change measurement unit 37 can measure a rate of change of the gas region R1 or the gas condition in the pressing period set by the pressing period setting unit 36, for example. In this case, the gas change measurement unit 37 can measure any one of a rate of change of the area of the region having brightness equal to or lower than the predetermined threshold value in the ultrasound image U, a rate of change of the image quality of the site shown on the deeper side than the intestinal tract of the subject in the ultrasound image U, a rate of change of the coverage degree of the gas, a rate of change of the benign degree of the gas, and the like, as the rate of change of the gas region R1 or the gas condition.

Figure 6:
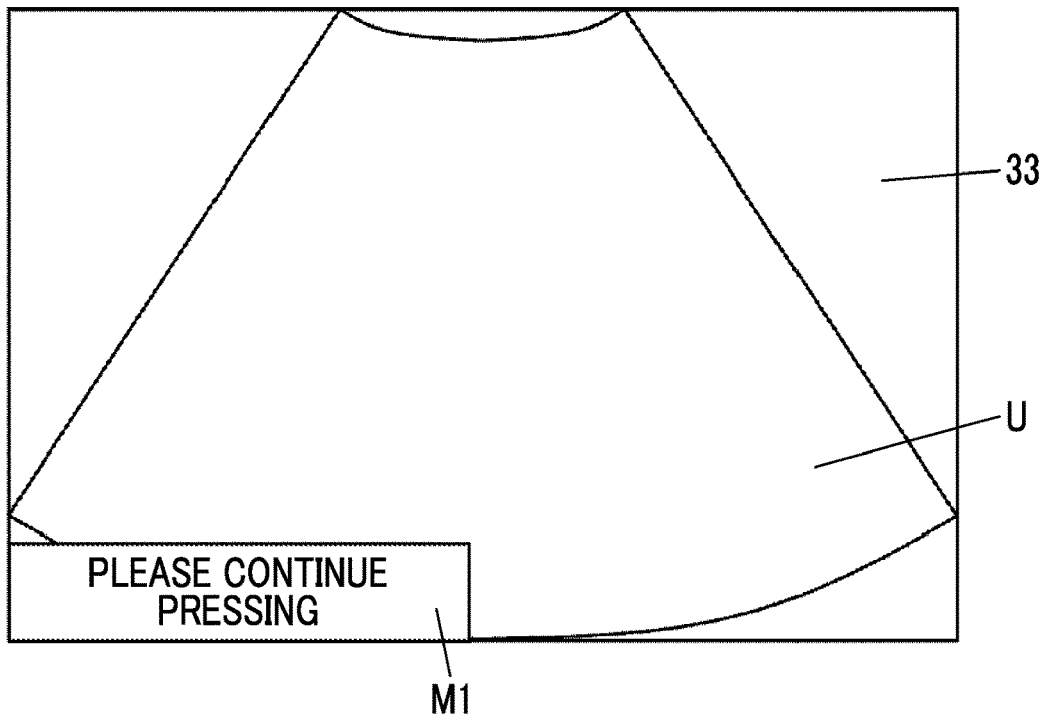
FIG. 6 is a diagram illustrating an example of guidance on ultrasound image capturing in the first embodiment of the present invention.

The imaging guide unit 38 provides guidance on the ultrasound image capturing to the user on the basis of the change of the gas region R1 or the gas condition measured by the gas change measurement unit 37. For example, in a case where the area of the gas region R1 measured by the gas change measurement unit 37 is reduced or the gas condition measured by the gas change measurement unit 37 is improved, the imaging guide unit 38 can determine that the method of pressing the ultrasound probe 2 currently performed by the user is effective for removing the gas in the intestine of the subject, and provide guidance to the user to capture the ultrasound image U while continuing pressing the ultrasound probe 2 against the subject. In this case, the gas change measurement unit 37 can provide guidance by displaying a message M1 such as "please continue pressing" on the monitor 33, as illustrated in FIG. 6, for example.

Figure 7:
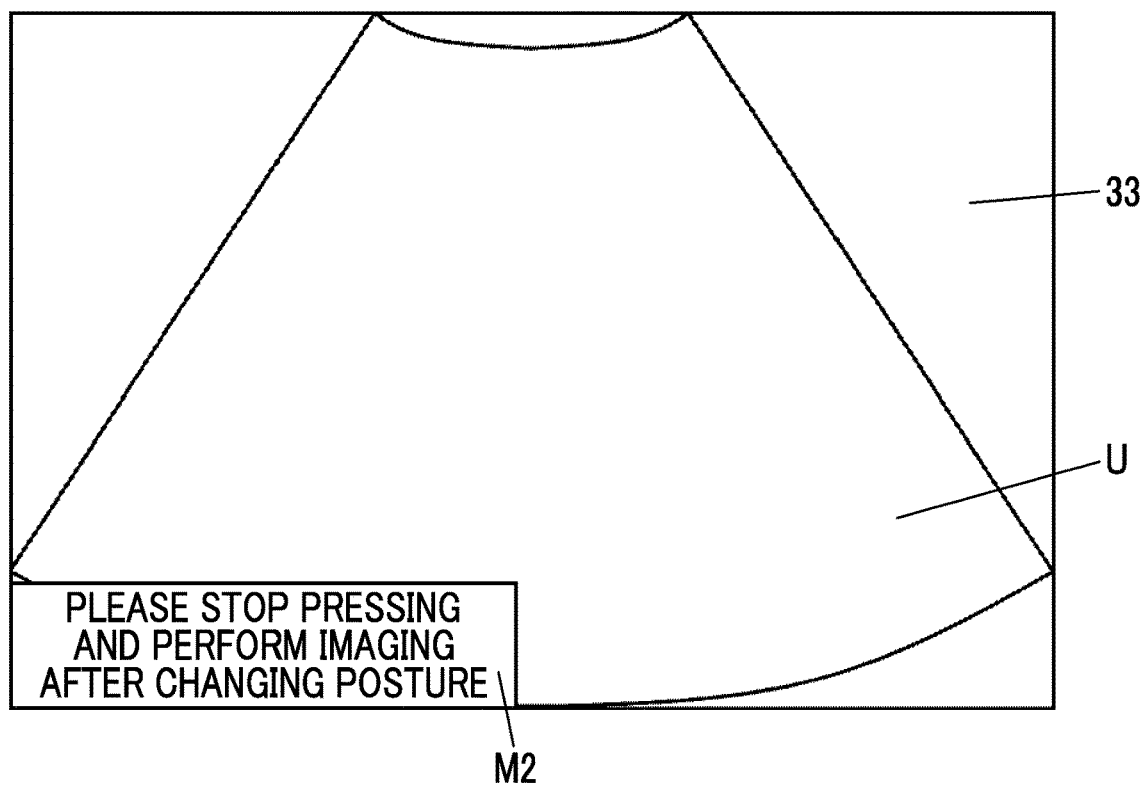
FIG. 7 is a diagram illustrating another example of guidance on ultrasound image capturing in the first embodiment of the present invention.

Further, in a case where the area of the gas region R1 or the gas condition measured by the gas change measurement unit 37 is not changed, the imaging guide unit 38 can determine that the method of pressing the ultrasound probe 2 currently performed by the user is not effective for removing the gas in the intestine of the subject, and provide guidance to the user to stop the pressing of the ultrasound probe 2 and to capture the ultrasound image U after changing the posture of the subject. In this case, the gas change measurement unit 37 can provide guidance by displaying a message M2 such as "please stop pressing and perform imaging after changing posture" on the monitor 33, as illustrated in FIG. 7, for example.

Here, the fact that the area of the gas region R1 or the gas condition is not changed means that the change of the gas region R1 or the gas condition measured by the gas change measurement unit 37 falls within a certain range. For example, in a case where the rate of change of the gas region R1 or the gas condition is measured by the gas change measurement unit 37, the fact that the area of the gas region R1 or the gas condition is not changed can be defined that the rate of change has a value within a predetermined range including zero.

The processor 41 having the image generation unit 31, the display controller 32, the gas specifying unit 35, the pressing period setting unit 36, the gas change measurement unit 37, the imaging guide unit 38, and the main body controller 39 is configured by a central processing unit (CPU) and a control program for causing the CPU to execute various kinds of processing, but the processor 41 may be configured by using a field programmable gate array (FPGA), a digital signal processor (DSP), an application specific integrated circuit (ASIC), a graphics processing unit (GPU), or other integrated circuits (IC) or may be configured by a combination thereof.

In addition, the image generation unit 31, the display controller 32, the gas specifying unit 35, the pressing period setting unit 36, the gas change measurement unit 37, the imaging guide unit 38, and the main body controller 39 of the processor 41 can also be configured by being integrated partially or entirely into one CPU or the like.

Next, the basic operation of the ultrasound diagnostic apparatus 1 according to the first embodiment will be described in detail using the flowchart illustrated in FIG. 8.

First, in Step S1, the user of the ultrasound diagnostic apparatus 1 brings the ultrasound probe 2 into contact with the body surface of the lower abdomen of the subject, and acquires the ultrasound image U in this state. In a case where the ultrasound image U is acquired, the transmission and reception circuit 22 performs so-called reception focusing processing under the control of the main body controller 39 to generate sound ray signals. The sound ray signals generated by the transmission and reception circuit 22 are sent to the image generation unit 31. The image generation unit 31 generates the ultrasound image U using the sound ray signals sent from the transmission and reception circuit 22. The ultrasound image U acquired in this manner is sent to the display controller 32, and is displayed on the monitor 33. Further, the ultrasound image U is stored in the image memory 34.

Next, in Step S2, the main body controller 39 determines whether or not the pressing of the ultrasound probe 2 against the subject is started. In this case, for example, in a case where an instruction to start the pressing of the ultrasound probe 2 is input by the user via the input device 40, the main body controller 39 can determine that the pressing of the ultrasound probe 2 is started. Further, for example, in a case where an instruction to start the pressing of the ultrasound probe 2 is not input by the user via the input device 40, the main body controller 39 can determine that the pressing of the ultrasound probe 2 is not started.

In a case where it is determined in Step S2 that the pressing of the ultrasound probe 2 is not started, the processing returns to Step S1, and a new ultrasound image U is acquired. In this manner, processing of Step S1 and Step S2 is repeated until it is determined in Step S2 that the pressing of the ultrasound probe 2 is started.

In a case where it is determined in Step S2 that the pressing of the ultrasound probe 2 is started, the processing proceeds to Step S3. From this point on, the user starts to press the ultrasound probe 2 against the subject. Thereafter, the user keeps pressing the ultrasound probe 2 against the subject.

In Step S3, the pressing period setting unit 36 sets the pressing period in which the ultrasound probe 2 is pressed against the subject. In this case, the pressing period setting unit 36 can store, for example, a predetermined time in advance, and set the time as the pressing period. The time set as the pressing period by the pressing period setting unit 36 can be set in advance by the user via the input device 40 before the examination on the subject is started.

In Step S4, the gas specifying unit 35 specifies the gas region R1 or the gas condition on the basis of the ultrasound image U acquired in latest Step S1. In this case, the gas specifying unit 35 can specify the gas region R1 or the gas condition by using the trained determination model obtained by learning calculating the area of the region having brightness equal to or lower than the predetermined threshold value in the ultrasound image U, calculating the image quality of the site shown on the deeper side than the intestinal tract of the subject in the ultrasound image U, and the gas region R1 or the gas condition in the ultrasound image U in which at least the lower abdomen of the subject is imaged, for example.

In Step S5, the main body controller 39 determines whether or not the pressing period set in Step S3 has elapsed. In a case where it is determined in Step S5 that the pressing period has not elapsed, the processing proceeds to Step S6.

In Step S6, similarly to Step S1, a new ultrasound image U is acquired. In a case where the processing of Step S6 is completed, the processing returns to Step S4.

As described above, the processing of Steps S4 to S6 is repeated until it is determined in Step S5 that the pressing period has elapsed. In a case where it is determined in Step S5 that the pressing period has elapsed, the processing proceeds to Step S7.

In Step S7, the gas change measurement unit 37 measures the change of the gas region R1 or the gas condition while the ultrasound probe 2 is pressed against the subject, on the basis of the specifying result of the gas region R1 or the gas condition, which is obtained for the plurality of frames of the ultrasound images U, which are continuous in time, by the repetition of Step S4 to Step S6 in the pressing period set in Step S3. In this case, for example, the gas change measurement unit 37 can measure the rate of change of the gas region R1 or the gas condition in the pressing period such as the rate of change of the area of the gas region R1 in the pressing period.

Finally, in Step S8, the imaging guide unit 38 provides guidance on the ultrasound image capturing to the user on the basis of the change of the gas region R1 or the gas condition measured in Step S7.

For example, in a case where the area of the gas region R1 measured in Step S7 is reduced or the gas condition measured in Step S7 is improved, the imaging guide unit 38 can determine that the method of pressing the ultrasound probe 2 currently performed by the user is effective for removing the gas in the intestine of the subject, and provide guidance by displaying the message M1 such as "please continue pressing" on the monitor 33, as illustrated in FIG. 6. The user checks the message M1, and continues the examination while continuing pressing the ultrasound probe 2 against the subject.

Further, in a case where the area of the gas region R1 or the gas condition measured in Step S7 is not changed, the imaging guide unit 38 can determine that the method of pressing the ultrasound probe 2 currently performed by the user is not effective for removing the gas in the intestine of the subject, and provide guidance by displaying the message M2 such as "please stop pressing and perform imaging after changing posture" on the monitor 33, as illustrated in FIG. 7. The user checks the message M2, and performs examination while pressing the ultrasound probe 2 against the subject again after stopping the pressing and changing the arrangement position of the ultrasound probe 2.

As described above, since guidance on the appropriate method of the ultrasound image capturing is provided to the user in Step S8 on the basis of the measurement result of the change of the gas region R1 or the gas condition in Step S7, even in a case where gas is accumulated in the intestine of the subject, the user can accurately observe the target site by sufficiently removing the gas regardless of the skill level, by checking the guidance in Step S8.

Figure 8:
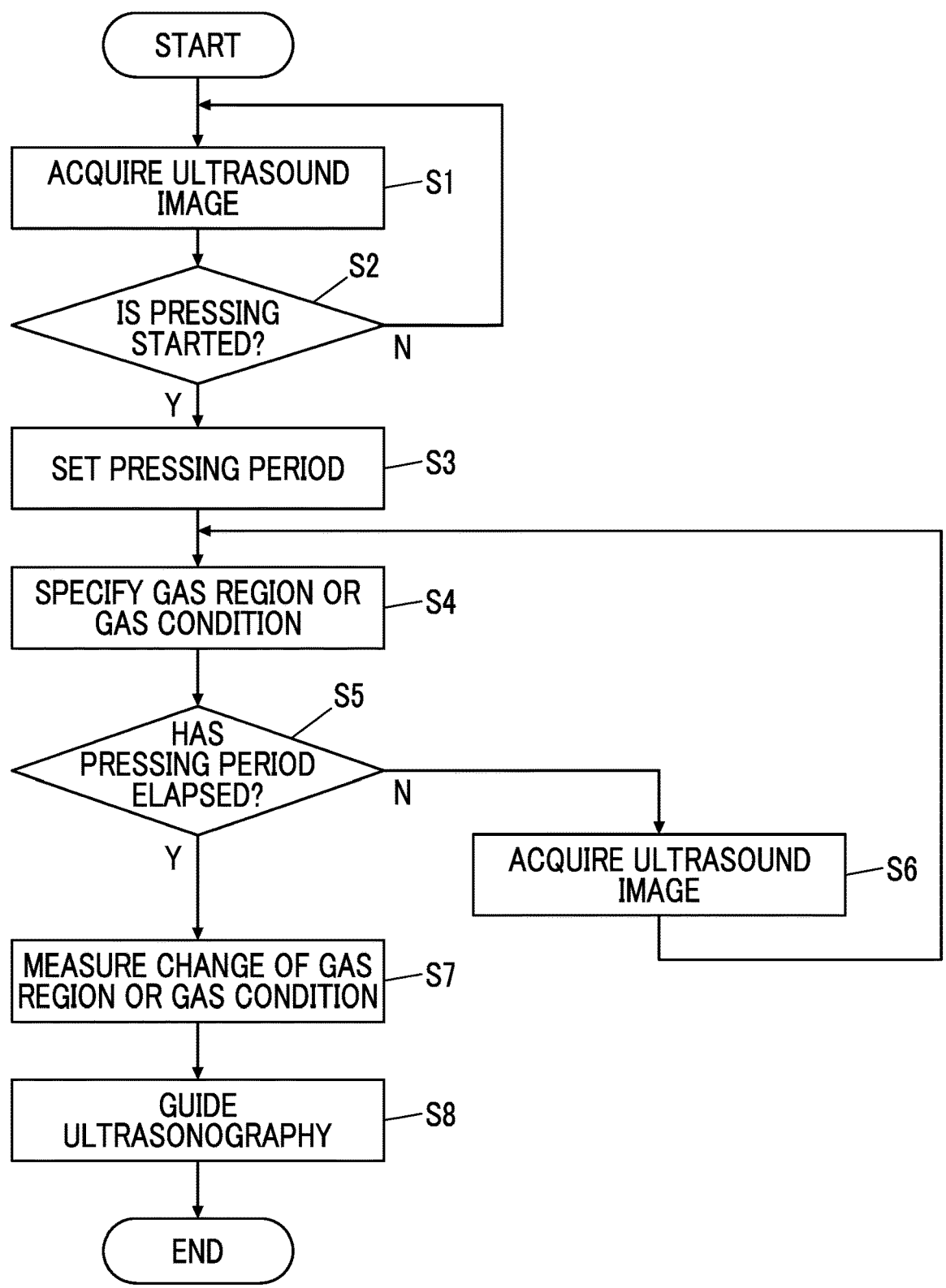
FIG. 8 is a flowchart illustrating an operation of the ultrasound diagnostic apparatus according to the first embodiment of the present invention.

In a case where the processing of Step S8 is completed, the operation of the ultrasound diagnostic apparatus 1 according to the flowchart of FIG. 8 is ended.

As described above, with the ultrasound diagnostic apparatus 1 according to the first embodiment of the present invention, the gas specifying unit 35 specifies the gas region R1 or the gas condition on the basis of the ultrasound image U, the gas change measurement unit 37 automatically measures the change of the gas region R1 or the gas condition in a case where the ultrasound probe 2 is pressed against the subject, the imaging guide unit 38 provides guidance on the ultrasound image capturing to the user on the basis of the change of the gas region R1 or the gas condition. Therefore, even in a case where gas is accumulated in the intestine of the subject, the target site can be accurately observed regardless of the user's skill level.

The description has been made in which the transmission and reception circuit 22 is included in the ultrasound probe 2, but the transmission and reception circuit 22 can be included in the apparatus main body 3 instead of being included in the ultrasound probe 2.

Further, the description has been made in which the image generation unit 31 is included in the apparatus main body 3, but the image generation unit 31 may be included in the ultrasound probe 2 instead of being included in the apparatus main body 3.

The description has been made in which the ultrasound probe 2 and the apparatus main body 3 are connected in a wired manner, but the ultrasound probe 2 and the apparatus main body 3 may be connected in a wireless manner.

In the image generation unit 31, the description has been made in which the DSC 52 is connected to the signal processing unit 51 and the image processing unit 53 is connected to the DSC 52, but the image processing unit 53 may be connected to the signal processing unit 51, and the DSC 52 may be connected to the image processing unit 53. In this case, after the image processing unit 53 performs predetermined processing such as gradation processing on the ultrasound image U generated by the signal processing unit 51, the ultrasound image U is raster-converted by the DSC 52. As described above, even in a case where the signal processing unit 51, the image processing unit 53, and the DSC 52 are connected in this order, similarly to the case where the signal processing unit 51, the DSC 52, and the image processing unit 53 are connected in this order, the ultrasound image U is generated by the image generation unit 31.

The description has been made in which the gas change measurement unit 37 measures the change of the gas region R1 or the gas condition specified by the gas specifying unit 35 during the pressing period set by the pressing period setting unit 36, but the gas change measurement unit 37 can measure the change of the gas region R1 or the gas condition specified by the gas specifying unit 35 before and after the pressing period in which the ultrasound probe 2 is pressed. In this case, the change of the gas region R1 or the gas condition measured by the gas change measurement unit 37 can be considered as an index representing how much gas in the intestine of the subject is removed by the user pressing the ultrasound probe 2 in the pressing period. Therefore, even in this case, the imaging guide unit 38 can determine whether or not the pressing of the ultrasound probe 2 currently performed by the user is effective for removing the gas on the basis of the change of the gas region R1 or the gas condition measured by the gas change measurement unit 37, and provide guidance on the ultrasound image capturing to the user.

Second Embodiment

In the first embodiment, the main body controller 39 determines whether or not the pressing of the ultrasound probe 2 against the subject is started on the basis of the user's instruction, but can detect a motion of the ultrasound probe 2 and automatically determine whether or not the pressing of the ultrasound probe 2 against the subject is started on the basis of the detected motion of the ultrasound probe 2. In the first embodiment, the description has been made in which the pressing period setting unit 36 sets the predetermined time as the pressing period, but the pressing period setting unit 36 can set the pressing period on the basis of the detected motion of the ultrasound probe 2.

Figure 9:
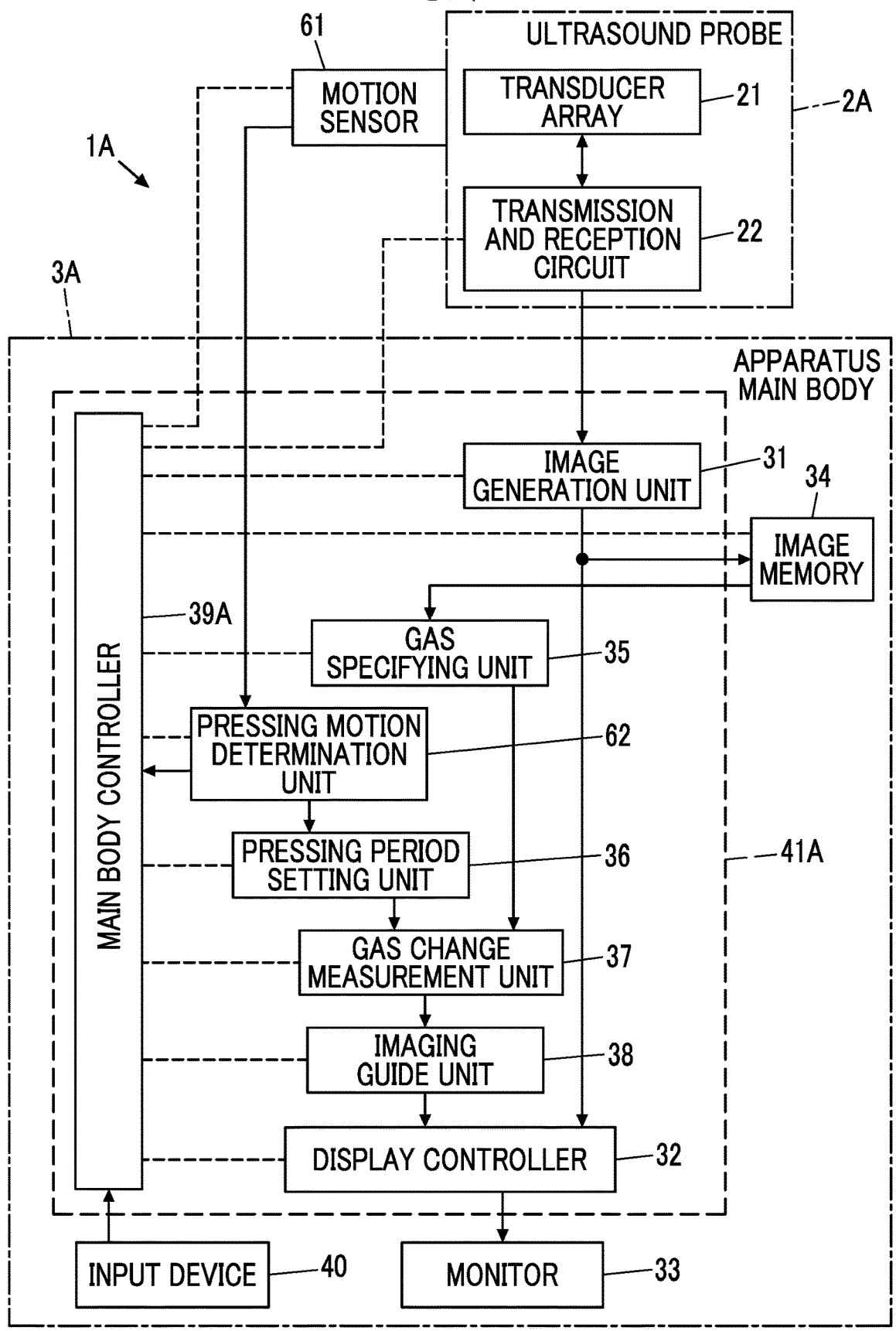
FIG. 9 is a block diagram illustrating a configuration of an ultrasound diagnostic apparatus according to a second embodiment of the present invention.

FIG. 9 illustrates a configuration of an ultrasound diagnostic apparatus 1A according to a second embodiment. The ultrasound diagnostic apparatus 1A is obtained by comprising an ultrasound probe 2A instead of the ultrasound probe 2 and comprising an apparatus main body 3A instead of the apparatus main body 3 in the ultrasound diagnostic apparatus 1 of the first embodiment illustrated in FIG. 1.

The ultrasound probe 2A is obtained by adding a motion sensor 61 to the ultrasound probe 2 in the first embodiment.

The apparatus main body 3A is obtained by adding a pressing motion determination unit 62 to the apparatus main body 3 in the first embodiment, and comprising a main body controller 39A instead of the main body controller 39. Further, the image generation unit 31, the display controller 32, the gas specifying unit 35, the pressing period setting unit 36, the gas change measurement unit 37, the imaging guide unit 38, the main body controller 39A, and the pressing motion determination unit 62 constitute a processor 41A for the apparatus main body 3A.

In the ultrasound diagnostic apparatus 1A, the motion sensor 61 is attached to the ultrasound probe 2A. The main body controller 39A and the pressing motion determination unit 62 of the apparatus main body 3A are connected to the motion sensor 61. Further, the pressing period setting unit 36 and the main body controller 39A are connected to the pressing motion determination unit 62.

The motion sensor 61 detects the motion of the ultrasound probe 2A. The motion sensor 61 is not particularly limited as long as the sensor can detect a three-dimensional motion of the ultrasound probe 2A, and for example, a 3-axis motion sensor consisting of a 3-axis acceleration sensor, a 6-axis motion sensor consisting of a combination of a 3-axis acceleration sensor and a so-called 3-axis gyro sensor, a 9-axis motion sensor consisting of a combination of a 3-axis acceleration sensor, a 3-axis gyro sensor, and a so-called 3-axis geomagnetic sensor, or the like can be used.

The pressing motion determination unit 62 determines a pressing motion of the ultrasound probe 2A against the subject on the basis of the motion of the ultrasound probe 2A detected by the motion sensor 61. Here, the pressing motion of the ultrasound probe 2A against the subject includes the start of the pressing of the ultrasound probe 2A, the pause during the pressing of the ultrasound probe 2A, and the end the pressing of the ultrasound probe 2A.

Figure 10:
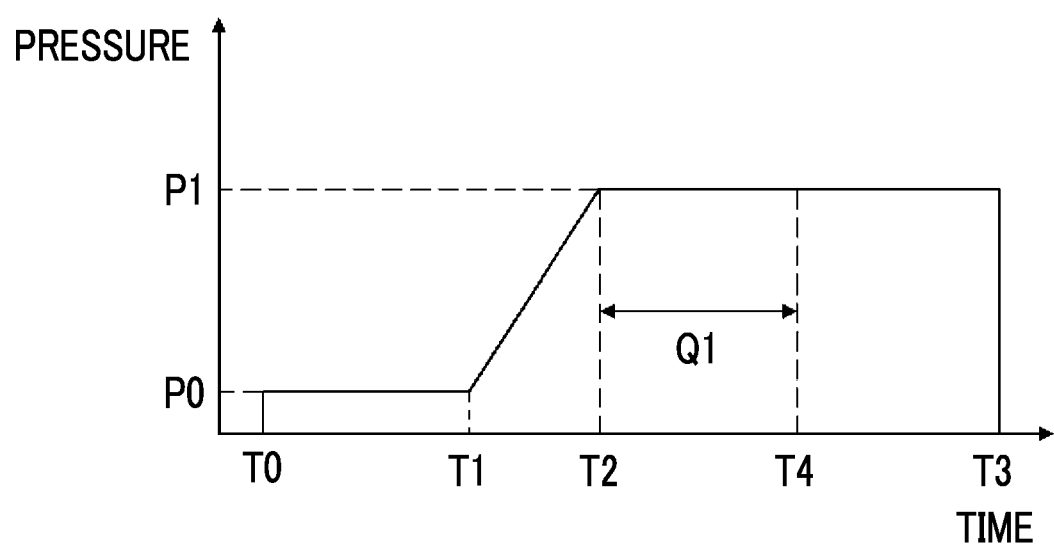
FIG. 10 is a diagram illustrating an example of a relationship between an elapse time and a pressure of an ultrasound probe that presses the subject.

FIG. 10 illustrates an example of a relationship between a pressure applied to the subject by the ultrasound probe 2A in a case where the ultrasound probe 2A is pressed against the subject, and an elapse time in the pressing of the ultrasound probe 2A. In this example, in order to capture the ultrasound image U representing the tomogram in the subject, the ultrasound probe 2A is brought into contact with the body surface of the subject at time point T0. At this time, a pressure P0 due to the weight of the ultrasound probe 2A is applied to the body surface of the subject. At time point T1, the pressing of the ultrasound probe 2A against the subject is started. The pressure applied to the body surface of the subject is gradually increased with time, and saturates at pressure P1 at time point T2. Thereafter, the pressing of the ultrasound probe 2A continues at constant pressure P1, and the pressing of the ultrasound probe 2A is ended at time point T3. In this example, since the ultrasound probe 2A is separated from the body surface of the subject at time point T3, the pressure at time point T3 is zero.

At time point T1, the ultrasound probe 2A begins to be displaced in a direction toward the deep portion of the subject (deep portion direction). Therefore, for example, in a case where the motion sensor 61 detects that the ultrasound probe 2A begins to be displaced in the deep portion direction, the pressing motion determination unit 62 can determine the start of the pressing of the ultrasound probe 2A.

At time point T2, the displacement of the ultrasound probe 2A in the deep portion direction is stopped, and thereafter, the ultrasound probe 2A is not displaced in the depth direction until time point T3. Therefore, in a case where the motion sensor 61 detects that the displacement of the ultrasound probe 2A, which has been displaced in the deep portion direction, in the deep portion direction is stopped, the pressing motion determination unit 62 can detect the pause during the pressing of the ultrasound probe 2A. For example, in a case where the motion sensor 61 detects that the displacement of the ultrasound probe 2A, which has been displaced in the deep portion direction, in the deep portion direction is stopped and the ultrasound probe 2A is not displaced in the depth direction until a certain time elapses, the pressing motion determination unit 62 can detect the pause during the pressing of the ultrasound probe 2A.

Further, at time point T3, the ultrasound probe 2A is displaced in a direction opposite to the deep portion direction of the subject, that is, in a direction separated from the body surface of the subject. Therefore, for example, in a case where the motion sensor 61 detects that the ultrasound probe 2A is displaced in the direction separated from the body surface of the subject, the pressing motion determination unit 62 can determine the end of the pressing of the ultrasound probe 2A.

In a case where the pressing motion determination unit 62 determines the start of the pressing of the ultrasound probe 2A, the main body controller 39A can automatically instruct each unit of the ultrasound diagnostic apparatus 1A to determine that the pressing of the ultrasound probe 2A against the subject is started, specify the gas region R1 or the gas condition in the ultrasound image U, set the pressing period, measure the change of the gas region R1 or the gas condition in the pressing period, and provide guidance on the ultrasound image capturing to the user on the basis of the change of the gas region R1 or the gas condition. Thereby, the user's trouble of operating the input device 40 for instructing the start of the pressing of the ultrasound probe 2A can be saved, and therefore, the user can smoothly perform an examination.

The pressing period setting unit 36 can set a period from when the pressing motion determination unit 62 determines the start of the pressing of the ultrasound probe 2A until the pressing motion determination unit 62 determines the end of the pressing of the ultrasound probe 2A, as the pressing period. That is, the pressing period setting unit 36 can set a period from time point T1 to time point T3 as the pressing period, for example, in the example of FIG. 10. The gas change measurement unit 37 measures the change of the gas region R1 or the gas condition using the pressing period set in this manner. Thereby, since the change of the gas region R1 or the gas condition in the period in which the pressing of the ultrasound probe 2A is actually performed is reliably measured, the measurement accuracy of the change of the gas region R1 or the gas condition can be improved.

The pressing period setting unit 36 can set a period from when the pressing motion determination unit 62 determines the start of the pressing of the ultrasound probe 2A until a predetermined time elapses after the pressing motion determination unit 62 determines the pause of the ultrasound probe 2A, as the pressing period. That is, the pressing period setting unit 36 can set a period from time point T1 to time point T4 as the pressing period by setting the time point when a predetermined time Q has elapsed from time point T2 as time point T4 in the example of FIG. 10, for example. Even in this case, since the change of the gas region R1 or the gas condition in the period in which the pressing of the ultrasound probe 2A is actually performed is reliably measured, the measurement accuracy of the change of the gas region R1 or the gas condition can be improved.

As described above, with the ultrasound diagnostic apparatus 1A according to the second embodiment of the present invention, the pressing motion determination unit 62 can determine the pressing motion of the ultrasound probe 2A on the basis of the motion of the ultrasound probe 2A detected by the motion sensor 61, and in a case where the pressing motion determination unit 62 determines the start of the pressing of the ultrasound probe 2A, the main body controller 39A can automatically instruct each unit of the ultrasound diagnostic apparatus 1A to determine that the pressing of the ultrasound probe 2A against the subject is started, specify the gas region R1 or the gas condition in the ultrasound image U, set the pressing period, measure the change of the gas region R1 or the gas condition in the pressing period, and provide guidance on the ultrasound image capturing to the user on the basis of the change of the gas region R1 or the gas condition. Therefore, the user's trouble of operating the input device 40 for instructing the start of the pressing of the ultrasound probe 2A can be saved, and therefore, the user can smoothly perform an examination.

Further, with the ultrasound diagnostic apparatus 1A according to the second embodiment of the present invention, since the pressing period setting unit 36 sets the pressing period on the basis of the pressing motion of the ultrasound probe 2A determined by the pressing motion determination unit 62, and the gas change measurement unit 37 reliably measures the change of the gas region R1 or the gas condition in the period in which the pressing of the ultrasound probe 2A is actually performed, the measurement accuracy of the change of the gas region R1 or the gas condition can be improved.

The motion sensor 61 may be attached to the outside of the housing (not illustrated) of the ultrasound probe 2A, or may be built in the ultrasound probe 2A.

Although not illustrated, instead of the motion sensor 61, a pressure sensor may be provided for detecting the pressure due to the pressing of the ultrasound probe 2A against the subject. In this case, the pressing motion determination unit 62 can acquire a relationship between the elapse time and the pressure detected by the pressure sensor as illustrated in FIG. 10, and determine the pressing motion of the ultrasound probe 2A on the basis of the relationship.

Third Embodiment

In the second embodiment, the description has been made in which the pressing motion determination unit 62 determines the pressing motion of the ultrasound probe 2A on the basis of the motion of the ultrasound probe 2A detected by the motion sensor 61, but the pressing motion of the ultrasound probe 2A can be determined by analyzing an optical image including at least the ultrasound probe 2A.

Figure 11:
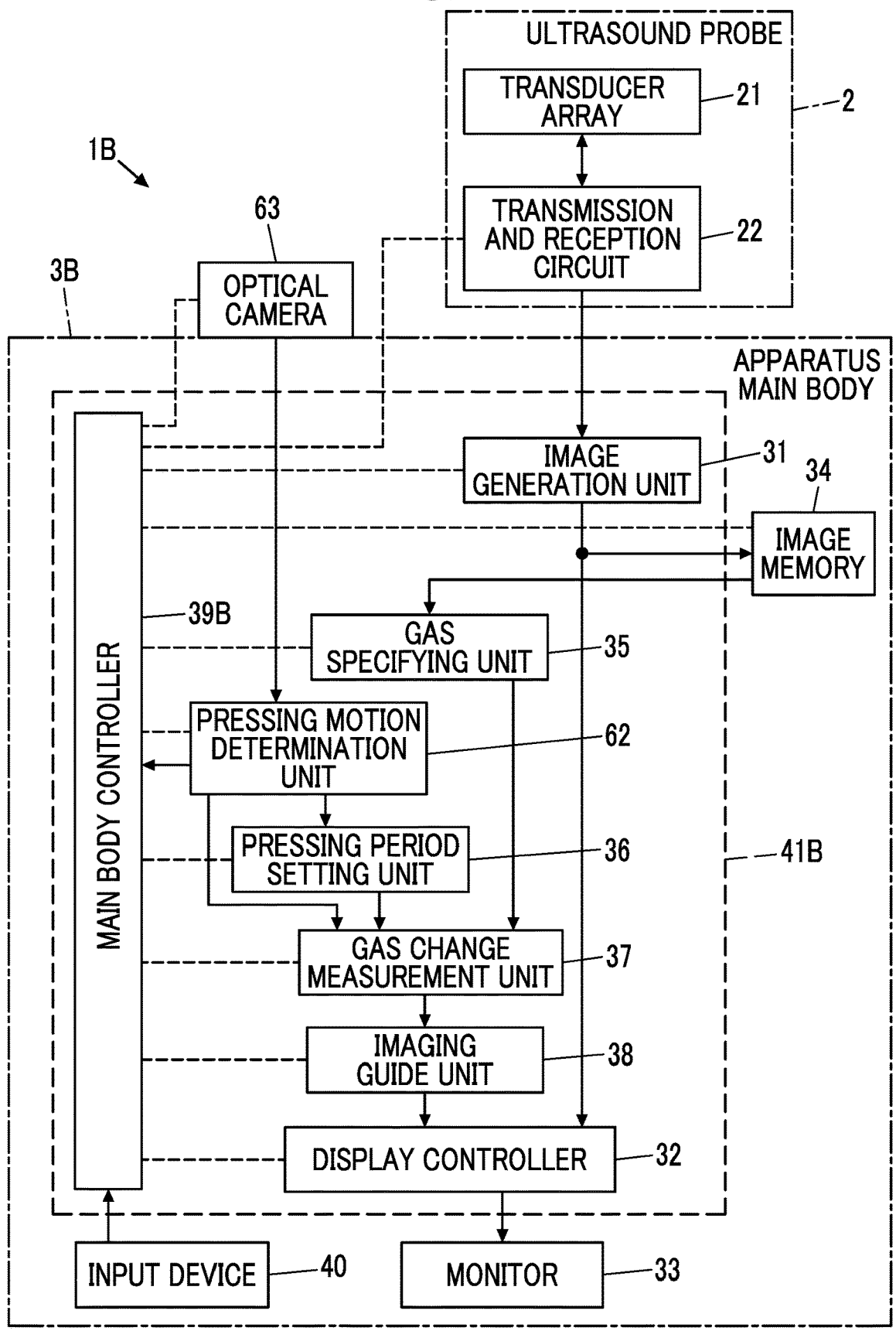
FIG. 11 is a block diagram illustrating a configuration of an ultrasound diagnostic apparatus according to a third embodiment of the present invention.

FIG. 11 illustrates a configuration of an ultrasound diagnostic apparatus 1B according to a third embodiment. The ultrasound diagnostic apparatus 1B is obtained by comprising an ultrasound probe 2 in the first embodiment instead of the ultrasound probe 2A and comprising an apparatus main body 3B instead of the apparatus main body 3A in the ultrasound diagnostic apparatus 1A of the second embodiment illustrated in FIG. 9.

The apparatus main body 3B is obtained by adding an optical camera 63 to the apparatus main body 3A in the second embodiment, and comprising a main body controller 39B instead of the main body controller 39A. Further, the image generation unit 31, the display controller 32, the gas specifying unit 35, the pressing period setting unit 36, the gas change measurement unit 37, the imaging guide unit 38, the main body controller 39B, and the pressing motion determination unit 62 constitute a processor 41B for the apparatus main body 3B.

In the ultrasound diagnostic apparatus 1B, the optical camera 63 is attached to the apparatus main body 3B, and is connected to the main body controller 39B and the pressing motion determination unit 62.

The optical camera 63 acquires an optical image including at least the ultrasound probe 2 under the control of the main body controller 39B. For example, in a case where the apparatus main body 3B is configured by a portable small terminal device such as a so-called tablet computer or a so-called smartphone, the user directs the optical camera 63 toward the ultrasound probe 2 by holding the apparatus main body 3B configured by a small terminal device with one hand while holding the ultrasound probe 2 with the other hand during the examination on the subject, for example. The optical camera 63 can capture an optical image in this state, and acquire the optical image including at least the ultrasound probe 2, for example.

The pressing motion determination unit 62 can determine the pressing motion of the ultrasound probe 2 by analyzing the optical image in which the ultrasound probe 2 is imaged. In this case, the pressing motion determination unit 62 can determine the pressing motion of the ultrasound probe 2 by using the trained determination model obtained by learning the motion of the ultrasound probe 2 in the optical images in which the ultrasound probe 2 is imaged, for example. In a case where the optical image is input, the trained determination model outputs the type of the pressing motion of the ultrasound probe 2 shown in the optical image.

Further, for example, the pressing motion determination unit 62 can construct the trained determination model by applying a machine learning method described in Csurka et al.: Visual Categorization with Bags of Keypoints, Proc. of ECCV Workshop on Statistical Learning in Computer Vision, pp. 59-74 (2004) or a general image recognition method using deep learning or so-called convolutional neural network (CNN) described in Krizhevsk et al.: ImageNet Classification with Deep Convolutional Neural Networks, Advances in Neural Information Processing Systems 25, pp. 1106-1114 (2012).

As described above, with the ultrasound diagnostic apparatus 1B according to the third embodiment of the present invention, since the pressing motion determination unit 62 can automatically determine the pressing motion of the ultrasound probe 2, similarly to the ultrasound diagnostic apparatus 1A of the second embodiment, the user's trouble of operating the input device 40 for instructing the start of the pressing of the ultrasound probe 2 can be saved, and therefore, the user can smoothly perform an examination. Further, since the pressing period setting unit 36 sets the pressing period on the basis of the pressing motion of the ultrasound probe 2 determined by the pressing motion determination unit 62, and the gas change measurement unit 37 reliably measures the change of the gas region R1 or the gas condition in the period in which the pressing of the ultrasound probe 2 is actually performed, the measurement accuracy of the change of the gas region R1 or the gas condition can be improved.

The description has been made in which the apparatus main body 3B is configured by a portable small terminal device such as a tablet computer or a smartphone, but the form of the apparatus main body 3B is not particularly limited, and the apparatus main body 3B may be, for example, a so-called stationary type. In this case, the optical camera 63 can be attached to the apparatus main body 3B so that the optical image including the ultrasound probe 2 can be acquired, for example.

Further, the optical camera 63 may not be fixed to the apparatus main body 3B. The optical camera 63 may be connected to the apparatus main body 3B in a wired or wireless manner, and may be independent of the apparatus main body 3B.

EXPLANATION OF REFERENCES 1, 1A, 1B: ultrasound diagnostic apparatus
2, 2A: ultrasound probe
3, 3A, 3B: apparatus main body
21: transducer array
22: transmission and reception circuit
23: pulser
24: amplification unit
25: AD conversion unit
26: beam former
31: image generation unit
32: display controller
33: monitor
34: image memory
35: gas specifying unit
36: pressing period setting unit
37: gas change measurement unit
38: imaging guide unit
39, 39A, 39B: main body controller
40: input device
41, 41A, 41B: processor
51: signal processing unit
52: DSC
53: image processing unit
61: motion sensor
62: pressing motion determination unit
63: optical camera
A1: kidney
A2: liver
A3: bladder
A4: uterus
M1, M2: message
P1, P2: pressure
Q1: period
R1: gas region
T1, T2, T3, T4: time point
U: ultrasound image

What is claimed is:

1. An ultrasound diagnostic apparatus comprising:
an ultrasound probe;
a processor configured to
perform transmission and reception of ultrasound beams using the ultrasound probe,
acquire a plurality of frames of ultrasound images which are continuous in time and in which a lower abdomen of a subject is imaged;
specify a gas region or a gas condition based on the ultrasound image;
once the ultrasound probe is pressed against the subject, measure a change of the specified gas region or the specified gas condition in a pressing period where the ultrasound probe has been pressed, or before and after the pressing period; and
provide guidance on ultrasound image capturing based on the change of the gas region or the gas condition.

2. The ultrasound diagnostic apparatus according to claim 1,
wherein the processor is further configured to
set a predetermined time period as the pressing period, and
measure the change of the gas region or the gas condition in the pressing period.

3. The ultrasound diagnostic apparatus according to claim 2,
wherein the processor is further configured to measure a rate of change of the gas region or the gas condition in the pressing period.

4. The ultrasound diagnostic apparatus according to claim 2,
wherein the processor is further configured to
determine a pressing motion of the ultrasound probe against the subject based on a motion of the ultrasound probe, and
measure the change of the gas region or the gas condition once the pressing of the ultrasound probe is determined.

5. The ultrasound diagnostic apparatus according to claim 3,
wherein the processor is further configured to
determine a pressing motion of the ultrasound probe against the subject based on a motion of the ultrasound probe, and
measure the change of the gas region or the gas condition once the pressing of the ultrasound probe is determined.

6. The ultrasound diagnostic apparatus according to claim 4, further comprising:
a motion sensor configured to detect a motion of the ultrasound probe,
wherein the processor is further configured to determine the pressing motion based on the motion of the ultrasound probe detected by the motion sensor.

7. The ultrasound diagnostic apparatus according to claim 4, further comprising:
an optical camera configured to acquire an optical image including at least the ultrasound probe,
wherein the processor is further configured to determine the pressing motion by analyzing the optical image acquired by the optical camera.

8. The ultrasound diagnostic apparatus according to claim 7,
wherein the processor is further configured to determine the pressing motion of the ultrasound probe by using a trained determination model obtained by learning the motion of the ultrasound probe in the optical image in which the ultrasound probe is imaged.

9. The ultrasound diagnostic apparatus according to claim 4, wherein the processor is further configured to determine a start of the pressing of the ultrasound probe and an end of the pressing of the ultrasound probe as the pressing motion, and set a period from when the start of the pressing of the ultrasound probe is determined until the end of the pressing of the ultrasound probe is determined, as the pressing period.

10. The ultrasound diagnostic apparatus according to claim 6, wherein the processor is further configured to determine a start of the pressing of the ultrasound probe and an end of the pressing of the ultrasound probe as the pressing motion, and set a period from when the start of the pressing of the ultrasound probe is determined until the end of the pressing of the ultrasound probe is determined, as the pressing period.

11. The ultrasound diagnostic apparatus according to claim 4, wherein the processor is further configured to determine a start of the pressing of the ultrasound probe and a pause during the pressing of the ultrasound probe as the pressing motion, and set a period from when the start of the pressing of the ultrasound probe is determined until a predetermined time elapses after the pause of the ultrasound probe is determined, as the pressing period.

12. The ultrasound diagnostic apparatus according to claim 6, wherein the processor is further configured to determine a start of the pressing of the ultrasound probe and a pause during the pressing of the ultrasound probe as the pressing motion, and set a period from when the start of the pressing of the ultrasound probe is determined until a predetermined time elapses after the pause of the ultrasound probe is determined, as the pressing period.

13. The ultrasound diagnostic apparatus according to claim 1, wherein the processor is further configured to specify the gas region or the gas condition by calculating an area of a region having brightness equal to or lower than a predetermined threshold value in the ultrasound image.

14. The ultrasound diagnostic apparatus according to claim 2, wherein the processor is further configured to specify the gas region or the gas condition by calculating an area of a region having brightness equal to or lower than a predetermined threshold value in the ultrasound image.

15. The ultrasound diagnostic apparatus according to claim 1, wherein the processor is further configured to specify the gas region or the gas condition based on an image quality of a site shown on a deeper side than an intestinal tract of the subject in the ultrasound image.

16. The ultrasound diagnostic apparatus according to claim 1, wherein the processor is further configured to specify the gas region or the gas condition by using a trained determination model obtained by learning the gas region or the gas condition in the ultrasound image in which at least the lower abdomen is imaged.

17. The ultrasound diagnostic apparatus according to claim 1, wherein the processor is further configured to provide guidance to capture the ultrasound image while continuing the pressing of the ultrasound probe in a case where an area of the gas region which is measured is reduced or the gas condition which is measured is improved.

18. The ultrasound diagnostic apparatus according to claim 1, wherein the processor is further configured to provide guidance to stop the pressing of the ultrasound probe and to capture the ultrasound image after changing a posture of the subject in a case where an area of the gas region or the gas condition which is measured is not changed.

19. The ultrasound diagnostic apparatus according to claim 1, further comprising:

a monitor configured to display the ultrasound image.

20. A control method of an ultrasound diagnostic apparatus, the control method comprising:

performing transmission and reception of ultrasound beams using an ultrasound probe, and acquiring a plurality of frames of ultrasound images which are continuous in time and in which a lower abdomen of a subject is imaged;

specifying a gas region or a gas condition on the basis of the ultrasound image;

once the ultrasound probe is pressed against the subject, measuring a change of the specified gas region or the specified gas condition in a pressing period where the ultrasound probe has been pressed, or before and after the pressing period; and providing guidance on ultrasound image capturing on the basis of the measured change of the gas region or the gas condition.

* * * * *